United States Patent
Carrell et al.

(10) Patent No.: US 9,240,046 B2
(45) Date of Patent: Jan. 19, 2016

(54) METHOD AND SYSTEM TO ASSIST 2D-3D IMAGE REGISTRATION

(71) Applicants: King's College London, London (GB); Guy's & St. Thomas' NHS Foundation Trust, London (GB)

(72) Inventors: Tom Carrell, London (GB); Andreas Varnavas, London (GB); Graeme Penney, London (GB)

(73) Assignee: Cydar Limited, Cambridgeshire (GB)

( * ) Notice: Subject to any disclaimer, the term of this patent is extended or adjusted under 35 U.S.C. 154(b) by 0 days.

(21) Appl. No.: 14/382,999

(22) PCT Filed: Mar. 1, 2013

(86) PCT No.: PCT/GB2013/050515
§ 371 (c)(1),
(2) Date: Sep. 4, 2014

(87) PCT Pub. No.: WO2013/132235
PCT Pub. Date: Sep. 12, 2013

(65) Prior Publication Data
US 2015/0043798 A1 Feb. 12, 2015

(30) Foreign Application Priority Data
Mar. 5, 2012 (GB) .................................. 1203883.2

(51) Int. Cl.
*G06K 9/36* (2006.01)
*G06T 7/00* (2006.01)
*A61B 6/00* (2006.01)

(52) U.S. Cl.
CPC .............. *G06T 7/0012* (2013.01); *A61B 6/5223* (2013.01); *G06T 7/0042* (2013.01); *G06T 2207/10064* (2013.01); *G06T 2207/10081* (2013.01); *G06T 2207/30012* (2013.01)

(58) Field of Classification Search
USPC ......... 382/285, 294, 154, 130, 131, 128, 151, 382/173, 190, 224, 239, 299, 300, 301; 358/1.2, 403; 345/472; 375/E7.088; 715/850
See application file for complete search history.

(56) References Cited

U.S. PATENT DOCUMENTS 6,556,713 B2 * 4/2003 Kobayashi et al. ........... 382/224
6,668,101 B2 * 12/2003 Kaneda ......................... 382/301
(Continued)

FOREIGN PATENT DOCUMENTS

WO 2008078259 A2 7/2008

OTHER PUBLICATIONS

Ehm M et al., Automated vertebra identification in CT images, Proceedings of SPIE, International Society for Optical Engineering, US, vol. 7259, Mar. 27, 2009, pp. 72590B-1-11.
(Continued)

*Primary Examiner* — Anh Do
(74) *Attorney, Agent, or Firm* — McNeill Baur PLLC

(57) ABSTRACT

Embodiments of the invention provide a system and method that is able to automatically provide a starting point for 2D to 3D image registration, without relying on human recognition of features shown in the 2D image. This is achieved by preprocessing the 3D data to obtain synthetically generated 2D images of those parts of the 3D data volume which will be used for registration purposes. Many different synthetically generated 2D images of the or each part of the 3D volume are produced, each from a different possible viewing direction. Each of these synthetic images is then subject to a feature extraction process to extract characterizing feature data of the registration feature shown in the images. Once the feature extraction has been undertaken for each image, when registration is to be performed the real-time 2D image is processed by applying each of the sets of extracted features thereto, to try and identify which set best matches the registration features in the 2D image. For example, where a generalized Hough transform was used in the feature extraction, the R tables would be applied to the 2D image to obtain respective accumulation images. The accumulation images may then be ranked to identify which registration feature is shown in the 2-D image, and from which view direction. This gives the required information of which registration feature is being shown in the 2D image, and also the in-plane location and orientation. This information can then be used as a starting point for the 2D to 3D registration procedure.

20 Claims, 8 Drawing Sheets

Preoperative image processing workflow

(56) References Cited

U.S. PATENT DOCUMENTS

| | | | |
|---|---|---|---|
| 6,714,682 B2 * | 3/2004 | Kaneda | 382/239 |
| 6,972,865 B1 * | 12/2005 | Muramatsu | 358/1.2 |
| 7,889,905 B2 * | 2/2011 | Higgins et al. | 382/130 |
| 8,064,669 B2 * | 11/2011 | Higgins et al. | 382/130 |
| 8,675,935 B2 * | 3/2014 | Higgins et al. | 382/128 |
| 8,819,591 B2 * | 8/2014 | Wang et al. | 715/850 |

OTHER PUBLICATIONS

Graeme P Penney et al., A Comparison of Similarity Measures for Use in 2-D-3-D Medical Image Registration, IEEE Transactions on Medical Imaging, vol. 17, No. 4, Aug. 1, 1998, pp. 586-595.

Graeme Penney et al., An Image-Guided Surgery System to Aid Endovascular Treatment of Complex Aortic Aneurysms: Description and Initial Clinical Experience, Jun. 22, 2011, Information Processing in Computer-Assisted Interventions, Springer Berlin Heidelberg, Berlin, Heidelberg, pp. 13-24.

Howe B et al., Hierarchical segmentation of cervical and lumbar vertebrae using a customized generalized Hough transform and extensions to active appearance models, Image Analysis and Interpretation, 6th IEEE Southwest Symposium on IEEE, Jan. 1, 2004, pp. 182-186.

International Search Report and Written Opinion—PCT/GB2013/050515, Dated May 23, 2013.

* cited by examiner

Preoperative image processing workflow

Intraoperative image processing workflow

METHOD AND SYSTEM TO ASSIST 2D-3D IMAGE REGISTRATION

This is a 371 National Stage entry of pending International Application No. PCT/GB2013/050515, filed Mar. 1, 2013, which claims the benefit of GB 1203883.2, filed Mar. 5, 2012, all of which are incorporated herein by reference in their entirety.

TECHNICAL FIELD

The present invention relates to a technique used for assisting registration of 2D image data with 3D image data of the same area. Embodiments of the invention have particular application in image-guided surgery (IGS) systems, and in particular with the alignment of pre-obtained 3D imaging data with real time 2D imaging data obtained during surgery.

BACKGROUND TO THE INVENTION AND PRIOR ART

Registration of preoperative 3D data to 2D intraoperative fluoroscopy data has been widely proposed for a number of clinical applications. Systems for radiosurgery and neurosurgery are in widespread clinical use. These systems allow overlay of preoperative data onto interventional images or allow additional information from a preoperative Computerised Tomography (CT) scan (e.g. a radiotherapy plan) to be accurately aligned to the patient.

In more detail, prior to an operation a patient is typically subjected to a CT scan of the body area where the surgery will take place. This results in a three-dimensional image of the scanned body area. However, during surgery real time 2D fluoroscopy images are obtained of the same area, using for example a C-arm type fluoroscopy machine. However, a 2D fluoroscopy image may be insufficient to allow a surgeon to determine the precise position within the body of surgical instruments or surgical implants, particularly during catheter based MIS procedures. For example, during stent-graft repair of aortic aneurysms, precise stent placement is essential.

In order to address the drawbacks of the 2D images, it is known to augment the 2D real time image with the 3D pre-obtained image, obtained, for example from a CT scan. The problem then arises of ensuring accurate registration of the 3D image with the 2D image i.e. ensuring that the 2D image is aligned with the correct parts of the 3D image. FIG. 1 illustrates that CT position and orientation is defined by six rigid body parameters, being three translations X, Y, and Z, and three rotations $\theta x$, $\theta y$, and $\theta z$. These can be divided into parameters which define movements parallel to the plane of the fluoroscopy image (in plane parameters $\theta x$, Y, and Z), and parameters which define movements a component of which is normal to the fluoroscopy plane (out-of-plane parameters $\theta y$, and $\theta z$, and X). The registration problem is then one of how to manipulate these parameters such that the 3D data volume becomes aligned with the 2D image such that the surgeon can have some confidence in the registration achieved.

Various registration techniques are known in the art. Specifically, in Penney et al "An Image-Guided Surgery System to Aid Endovascular Treatment of Complex Aortic Aneurysms: Description and Initial Clinical Experience", IPCAI 2011, LNCS 6689, pp. 13-24 the present inventors describe an intensity based registration technique which requires a starting position to be chosen by relying on visual inspection and identification of a vertebra in the fluoroscopy image. FIG. 3(*a*) to (*c*) illustrate the procedure, where from an initial position (FIG. 3(*a*)) a region of interest is drawn (FIG. 3(*b*)) using a GUI, and the chosen 3D CT vertebra surface is then manually translated over the fluoroscopy vertebra (FIG. 3(*c*)).

The problem with this arrangement is that accurate vertebra identification can be difficult, particularly when neither the thorax nor the pelvis are visible. In this respect, many vertebrae can look the same, and unless the medical technician performing the registration is able to accurately identify which vertebra is shown on the fluoroscopy image then no accurate registration will be possible. The overall effect of this problem is that the time taken to achieve registration is usually increased, whilst the medical technician attempts to identify which vertebrae can be seen in the fluoroscopy image.

SUMMARY OF THE INVENTION

Embodiments of the invention are intended to address the above problem, by providing a system and method that is able to automatically provide a starting point for the 2D to 3D registration, without relying on human recognition of the features shown in the 2D image. This is achieved by pre-processing the 3D data to obtain synthetically generated 2D images of those parts of the 3D data volume which will be used for registration purposes. Many different synthetically generated 2D images of the or each part of the 3D volume are produced, each from a different possible viewing direction. Each of these synthetic images is then subject to a feature extraction process to extract characterising feature data of the registration feature shown in the images. For example, where a generalised Hough transform is to be used, the feature extraction comprises producing an R table for the registration feature. In many surgical embodiments the registration feature will be a vertebra, although it will be appreciated that almost any anatomical feature may be used, particularly those which are visible on fluoroscopy images.

Once the feature extraction has been undertaken for each image, when registration is to be performed prior or during surgery the real-time 2D image obtained, for example, via fluoroscopy is processed by applying each of the sets of extracted features thereto, to try and identify which set best matches the registration features in the 2D image. For example, where a generalised Hough transform was used in the feature extraction, the R tables would be applied to the 2D image to obtain respective accumulation images. The accumulation images may then be ranked to identify which registration feature is shown in the 2-D image, and from which view direction. This gives the required information of which registration feature is being shown in the fluoroscopy image, and also the in-plane location and orientation. This information can then be used as a starting point for the 2D to 3D registration procedure.

In view of the above, from one aspect the present invention provides a method of determining a start position for a 2D to 3D image registration, the method comprising: a) obtaining characteristic feature sets from a plurality of synthetic 2D images characterising one or more registration features imaged therein, the plurality of synthetic 2D images having been previously generated from the 3D image data set, the synthetic 2D images containing the one or more registration features having been previously imaged according to a plurality of respective viewing parameters; b) obtaining a 2D image to be registered with the 3D image data set; c) applying the characteristic feature sets to the obtained 2D image to locate one or more registration features therein; and d) determining which of the one or more characteristic features sets locate the one or more registration features in the obtained 2D image; wherein at least the viewing parameters relating to the synthetic image corresponding to the determined characteristic feature sets provide information relating to a start position for a subsequent registration of the obtained 2D image to the 3D image data set.

In one embodiment the information relating to the start position that is obtained is an identification per se of the registration featured (e.g., where vertebrae are used as registrations features, which vertebra is actually being displayed), as well as an in-plane location for the feature in the 2D image, and rotational orientation of the feature (determined from the viewing parameters, which include viewing angle). This then allows the corresponding features in the 3D image data set to be aligned with the 2D image features in accordance with the information, as a starting point for another registration process.

In one embodiment the registration features are one or more vertebrae. However, in other embodiments different registration features may be used. Specifically, in some embodiment the obtained 2D image is a fluoroscopy image, and hence in such embodiments the registration features may be any feature which can be discerned on a fluoroscopy image. For example, any skeletal or hard tissue feature which can be seen and discriminated on a fluoroscopy image may be suitable.

In one embodiment the 3D image data set is obtained via a computerised tomography (CT) scan, although other 3D scanning techniques may be used to obtain the 3D data set, such as magnetic resonance imaging (MRI), or ultrasound scanning.

In the preferred embodiment the characteristic feature sets are R tables for use with a generalised Hough transform. Here, the applying comprises generating accumulation images by applying the R-tables to the obtained 2D image using the generalised Hough transform. The use of R-tables and the generalised Hough transform is particularly suitable for identifying known registration features of a shape for which an R-table can be generated in advance.

In one embodiment the determining comprises ranking the accumulation images to determine which R table best locates the registration feature in the obtained 2D image. More specifically, in one embodiment the ranking comprises finding a normalised maximum pixel value in each accumulation image, and then sorting the accumulation images based on the normalised maximum pixel value to determine the image with the highest normalised intensity value. The image with the highest normalised intensity value is then selected, and the R table which produced that image identified. The DRR from which the identified R table was produced is then further identified, and the viewing parameters which generated the DRR then used as information relating to the start position for a subsequent 2D to 3D registration.

In another embodiment the first N (e.g. N=100) ranked accumulation images are found based on the normalised maximum intensity pixel values in each of the accumulation images. These N ranked accumulation images are then further processed as follows: A 2D-3D registration similarity measure (for example, gradient difference, Penney, G. P., Weese, J., Little, J. A., Desmedt, P., Hill, D. L. G. and Hawkes, D. J. "*A comparison of similarity measures for use in 2D-3D medical image registration*", IEEE Trans. Med. Imag., 1998, 17(4), 586-595) is used to calculate a similarity value between the 3D image data set (e.g. CT scan) and the obtained 2D image (e.g. fluoroscopy image) for each of the first N accumulation images found. The accumulation image associated with the maximum value calculated by the similarity measure determines the start position for a subsequent 2D to 3D registration. This enables the normalised maximum intensity pixel values in each of the accumulation images to find a set of likely candidate registration positions, while the more robust and accurate (but more computationally expensive) similarity measure is used to make the final selection of the accumulation image which best locates the registration feature.

In one embodiment there is further provided a step of checking that two or more registration features are located in the obtained 2D image. In this respect, if two or more registration features are present then it is possible to try to recognise each feature separately, and determine relevant viewing parameters for each. This then allows, for the two or more registration features, to check that the viewing parameters relating to the characteristic feature sets that located the registration features are within a predetermined distance of each other i.e. are similar to each other. If the correct viewing parameters have been obtained for each registration feature then they should be identical or very similar (within a small threshold distance) of each other.

Once a start position has been obtained (or at least information relating thereto obtained), in some embodiments there can then be performed an actual 2D to 3D image registration using the determined start position information. The registration can be an intensity based operation, as described by the inventors in there prior art paper ibid.

Once registration has been performed there can then be undertaken a check to check that registration parameters achieved for different registration features are within a predetermined distance. Again, different registration features should provide substantially the same registration parameters between the 2D and 3D images, and hence if widely different parameters are obtained from registrations performed on different features then there is a good chance that an error has occurred in at least one of the registrations. Conversely, if the registration parameters are substantially identical then one can be assured that accurate registration has been achieved.

In one embodiment a confidence value for the registration(s) may be calculated, and displayed to a user. This is particularly advantageous to the clinician, as he or she can be assured that correct registration has been achieved.

From another aspect there is provided a method of generating characteristic feature sets characterising a registration feature for use in the method of any of the preceding claims, the method comprising: a) generating a plurality of synthetic 2D images from a 3D image data set, the synthetic 2D images containing one or more registration features imaged according to a plurality of respective viewing parameters; b) generating characteristic feature sets from the synthetic 2D images characterising the registration features imaged therein; and c) storing the generated characteristic feature sets.

A further aspect of the invention provides an image guided surgical system, comprising: a 2D imaging system arranged in use to obtain a 2D image to be registered with a 3D image data set; and a processor, arranged in use to: a) receive characteristic feature sets from a plurality of synthetic 2D images characterising one or more registration features imaged therein, the plurality of synthetic 2D images having been generated from the 3D image data set, the synthetic 2D images containing the one or more registration features imaged according to a plurality of respective viewing parameters; b) apply the characteristic feature sets to the obtained 2D image to locate one or more registration features therein; and c) determine which of the one or more characteristic features sets locate the one or more registration features in the obtained 2D image; wherein the viewing parameters relating to the synthetic image corresponding to the determined characteristic feature sets provide information relating to a start position for registration of the obtained 2D image to the 3D image data set.

A yet further aspect provides a system for generating characteristic feature sets characterising a registration feature for use with the system of any of claim 16 or 17, the system comprising: a processor; and a computer readable storage medium, the computer readable storage medium storing one or more programs so arranged such that when executed by the processor it/they cause the processor to: a) generate a plurality of synthetic 2D images from a 3D image data set, the synthetic 2D images containing one or more registration features imaged according to a plurality of respective viewing parameters; b) generate characteristic feature sets from the synthetic 2D images characterising the registration features imaged therein; and c) store the generated characteristic feature sets.

Further aspects and features of the invention will be apparent from the appended claims.

BRIEF DESCRIPTION OF THE DRAWINGS

Further features and advantages of the present invention will become apparent from the following description of an embodiment thereof, presented by way of example only, and by reference to the drawings, wherein like reference numerals refer to like parts, and wherein.

DESCRIPTION OF THE EMBODIMENTS

The embodiment of the invention to be described has two stages. The first stage comprises image processing that is performed on a pre-operative 3D image obtained prior to surgery. The purpose of the first stage is to obtain characterising feature sets of possible registration features that may be found in the 2D operative image, from several different viewing angles. Once these have been obtained, they may then be used during the second, operative, stage to identify registration features found in the fluoroscopy image, to provide a starting point for registration.

Figure 9:
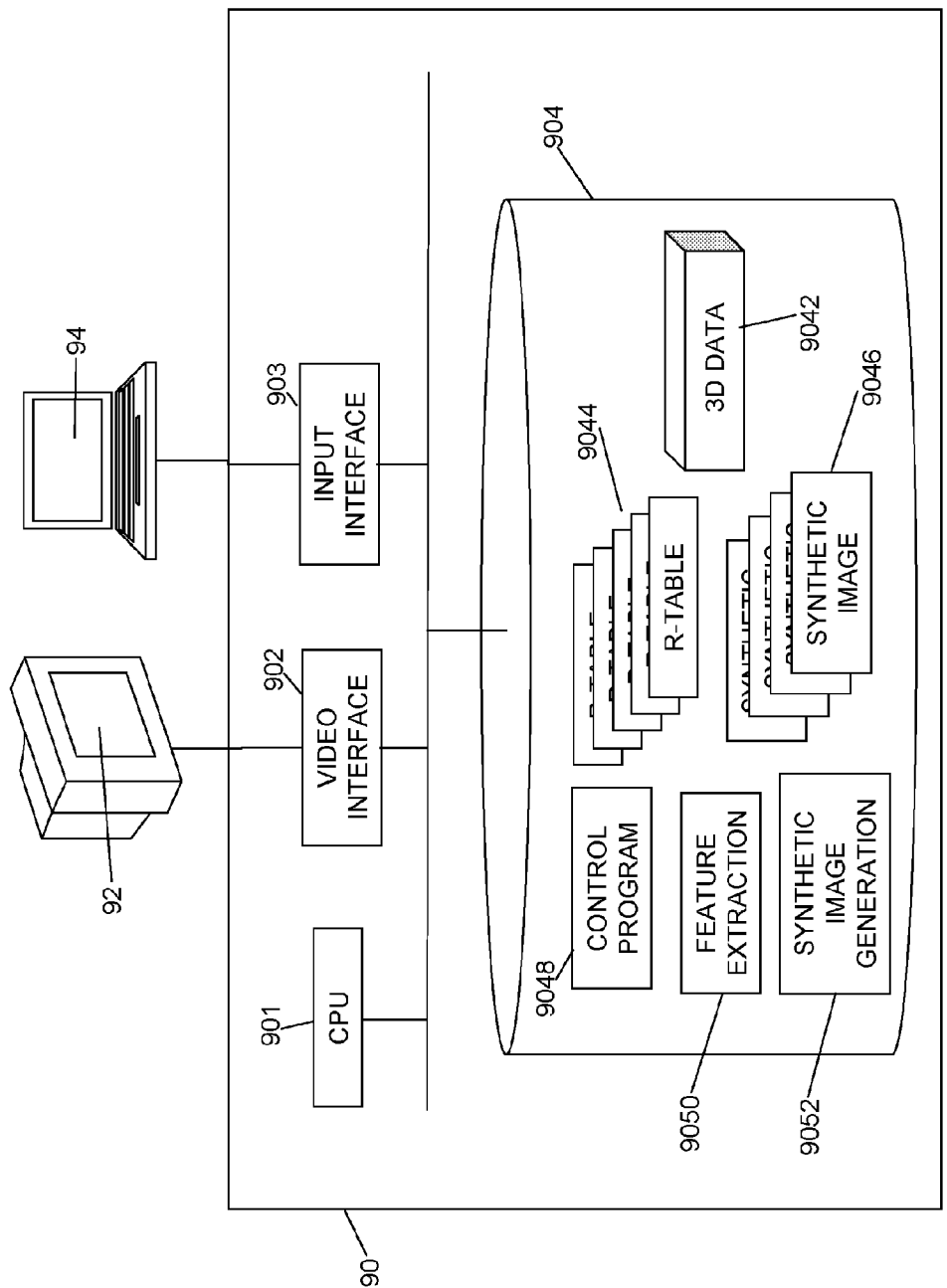
FIG. 9 is a diagram illustrating a computer system arranged to perform feature extraction in an embodiment of the invention.

FIG. 9 shows a general purpose computer system 90 having an output display 92 and user input features such as a keyboard 94 to allow control thereof. The computer comprises CPU 901, video interface 902 to control the display 92, and input interface 903 to receive user input from keyboard (or other input device) 94. Also provided is data storage medium 904, such as hard disk, solid state storage, or the like, upon which control programs and other data may be stored.

The data storage medium 904 stored thereon a control program 9048, that retains overall control of the computer 90 during the following procedures described below. Also stored thereon is a feature extraction program 9050 that acts under the control of the control program to extract characterising features of an image. Synthetic image generation program 9052 is also stored, and which is used to generate synthetic images, as described later. The input to the synthetic image generation program is 3D data 9042, obtained, for example, from a CT scan or the like. The synthetic images that are generated are stored as images 9046, and the extracted features from the images stored as data 9044. In one embodiment where a generalised Hough transform is to be used, the extracted features are R-tables 9044. An R table 9044 is obtained for each respective synthetic image 9046.

In the embodiment described below, the registration features that are to be found in the 2D images are vertebrae, and hence the synthetic images generated are images of individual vertebra generated from the 3D CT image thereof.

Figure 4:
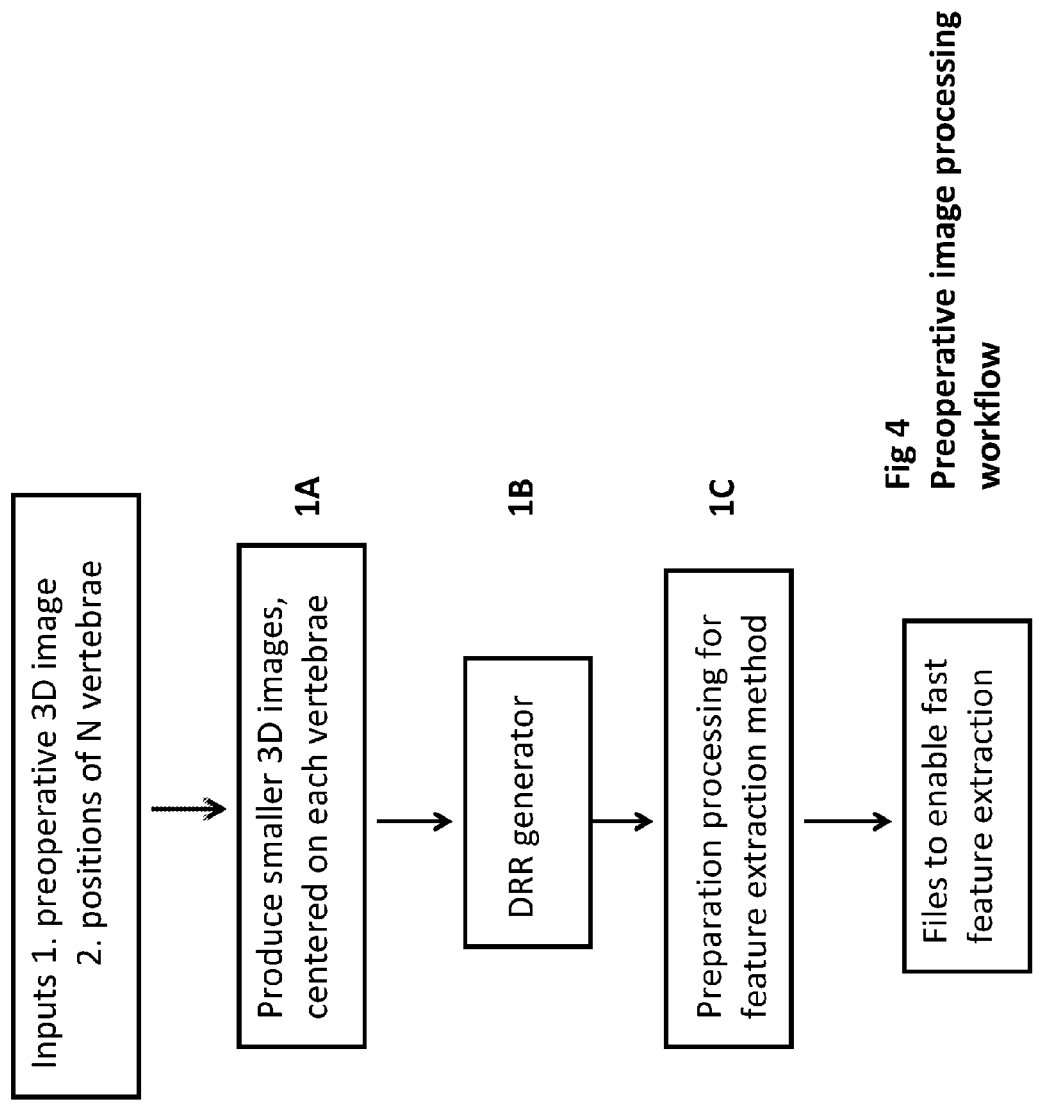
FIG. 4 is a flow diagram illustrating a feature extraction procedure of the present invention.

The operation of the first stage of the present embodiment is shown in FIG. 4. Here, the inputs are 1. the preoperative 3D image 9042 (e.g. computed tomography scan) and 2. positions of N vertebrae within the image, which can either be determined manually or using a segmentation algorithm. For abdominal operations, N could be 8 (for example, 5 lumbar vertebrae plus the 3 inferior thoracic vertebrae).

Step 1A first uses the vertebrae positions to produce N smaller 3D images centred on each vertebrae. That is, a 3D image is obtained of the vertebrae that are to be used as possible registration features.

Step 1B then takes each of the smaller 3D images and produces a large number of digitally reconstructed radiographs (DRRs), using the synthetic image generation program 9052. DRRs are synthetic x-ray images. DRRs will be produced for a wide variety of view directions, simulating the movement and settings on the fluoroscopy set and table to be used in the subsequent operation over a variety of imaging parameters, e.g. view angles, translations, magnification setting, focal length. For example if LAO/RAO angles +−48 degrees, Cranial caudial angle +−20 degrees and coronal plane angle +−20 degrees are all sampled at steps of 4 degrees this will result in production of 2904 DRRs per vertebra. Each DRR is stored as a synthetic image 9046.

Regarding how the DRRs are obtained, digitally reconstructed radiographs (DRRs) can be produced by casting rays through a CT volume. Each of these rays will go through a number of voxels. If the Hounsfield numbers of these voxels are integrated along the ray and projected onto an imaging plane then the resultant image will resemble a radiograph. Another technique to produce DRRs is known as "wobbled splatting", as described by Birkfellner W et al in *Wobbled splatting—a fast perspective volume rendering method for simulation of x-ray images from CT Phys Med Biol.* 2005 May 7; 50(9):N73-84. Epub 2005 Apr. 13. Any known method of producing DRRs may be used in an embodiment of the invention.

Figure 6:
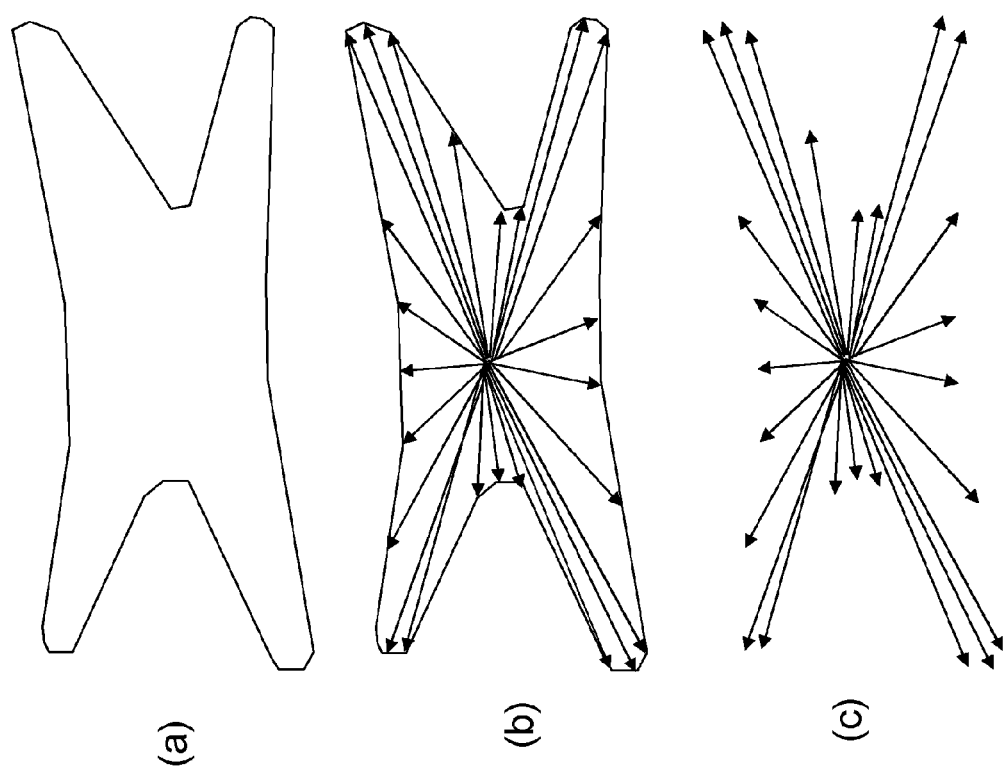
FIG. 6 is a series of diagrams illustrating feature extraction used in an embodiment of the invention.
Figure 7:
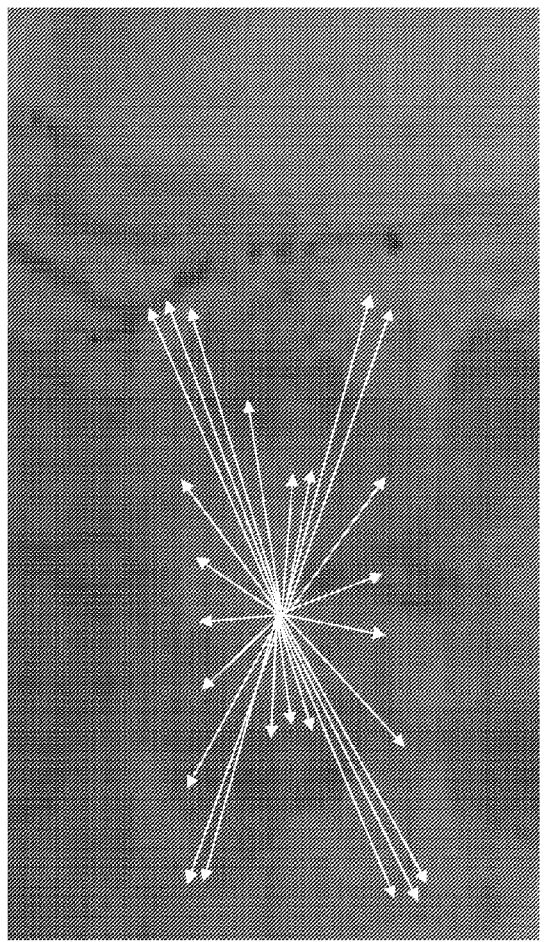
FIG. 7 is a diagram showing the application of a set of features to an image.

Step 1C then finally takes each of these DRRs and applies the required preparation processes for an image processing technique to allow fast and robust feature extraction of the feature shown within the DRR. This is performed by feature extraction program 9050. For example, if a generalised Hough transform were to be used, step 1C would produce an R-table for each DRR. FIG. 6 illustrates the production of an R table from each synthetic image. In FIG. 6(a) an edge detection algorithm or the like can be used to detect the edge of the vertebra in a synthetic image. A point (R) is then chosen within the image, and a number of vectors typically taken from the point to the edge lines to be characterised (FIG. 6(b)). The representation of these vectors then provides the R table (FIG. 6(c)). The R-table files are then stored as feature data sets 9044.

The feature data set files 9044 from step 1C which will enable fast feature extraction and determination of fluoroscopy view angle are the output from the preoperative image processing workflow, and are then subsequently transferred to the image guided surgical system for using in registration before or during the surgical procedure, as described next.

Figure 1:
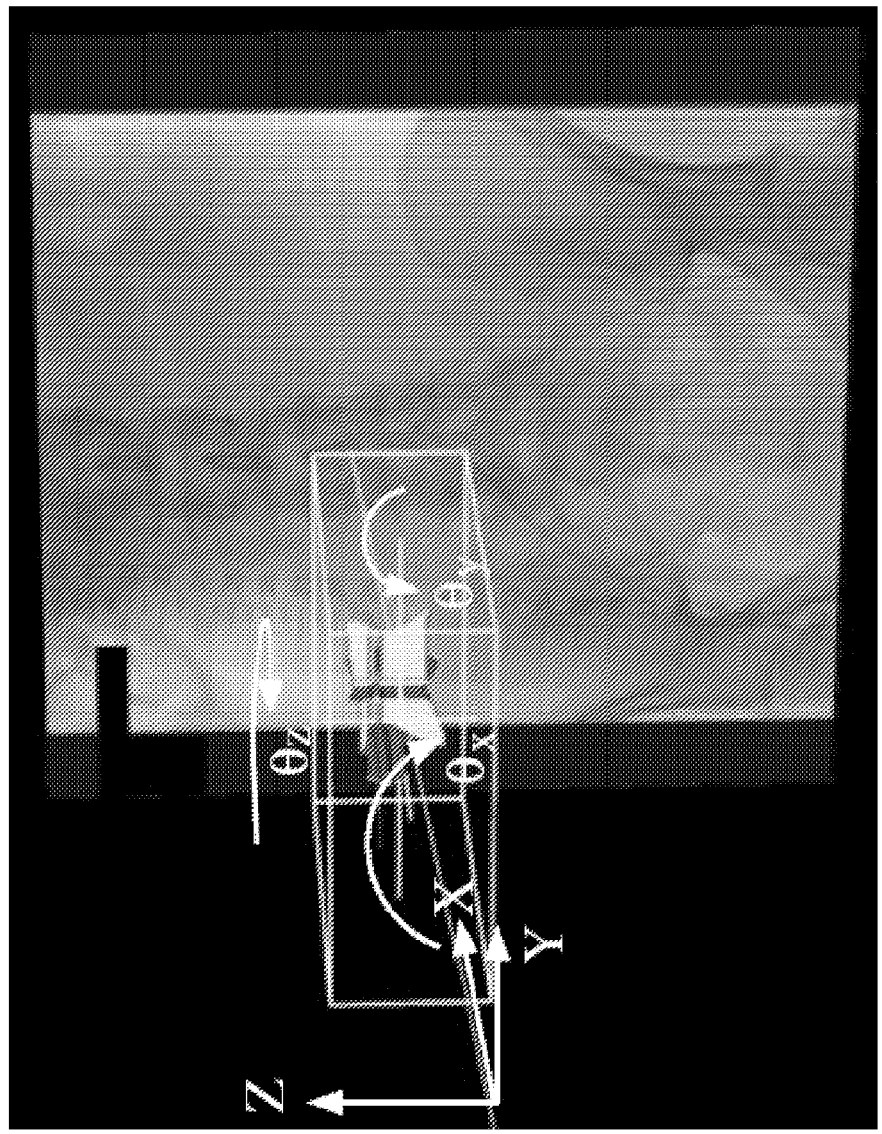
FIG. 1 is a diagram illustrating the orientation of 3D data.
Figure 2:
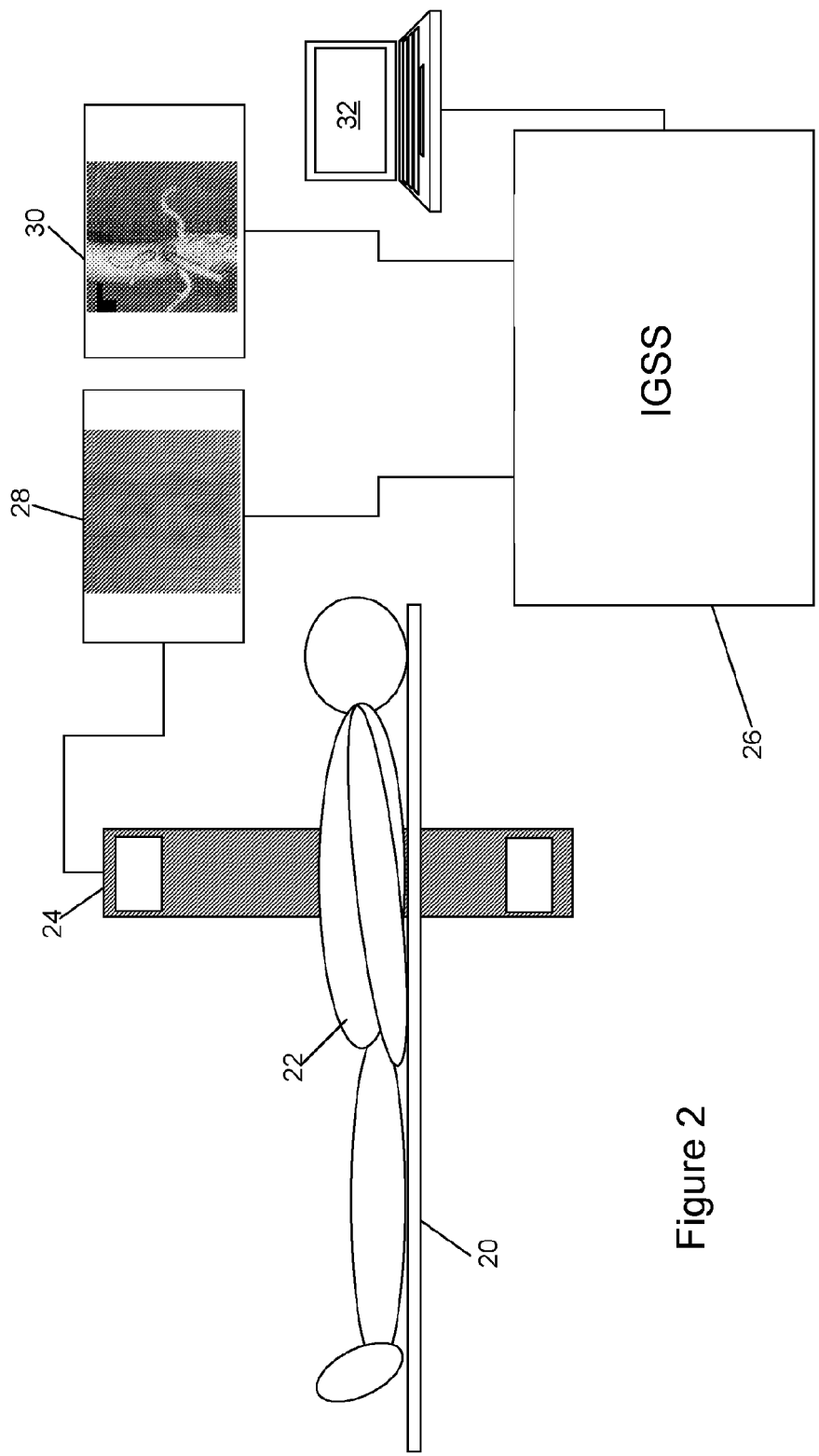
FIG. 2 is a block diagram of a typical surgical setup using a fluoroscopy machine.
Figure 3:
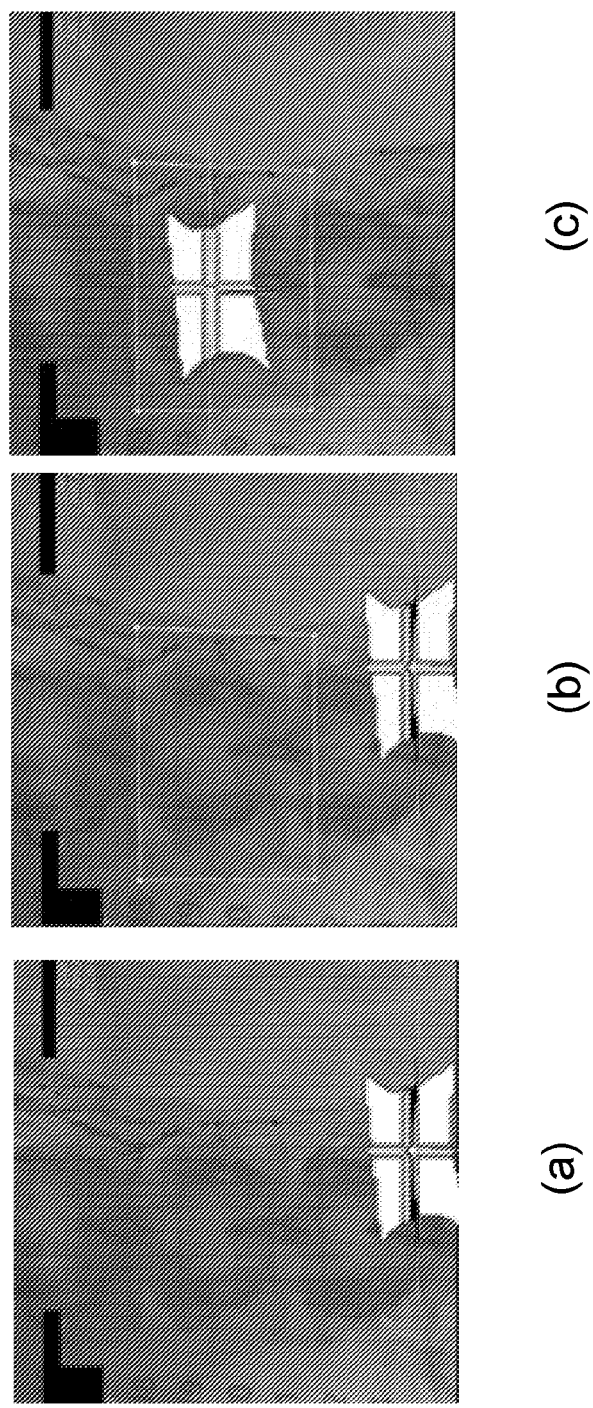
FIG. 3 is a series of diagrams illustrating a starting point procedure of the prior art.
Figure 5:
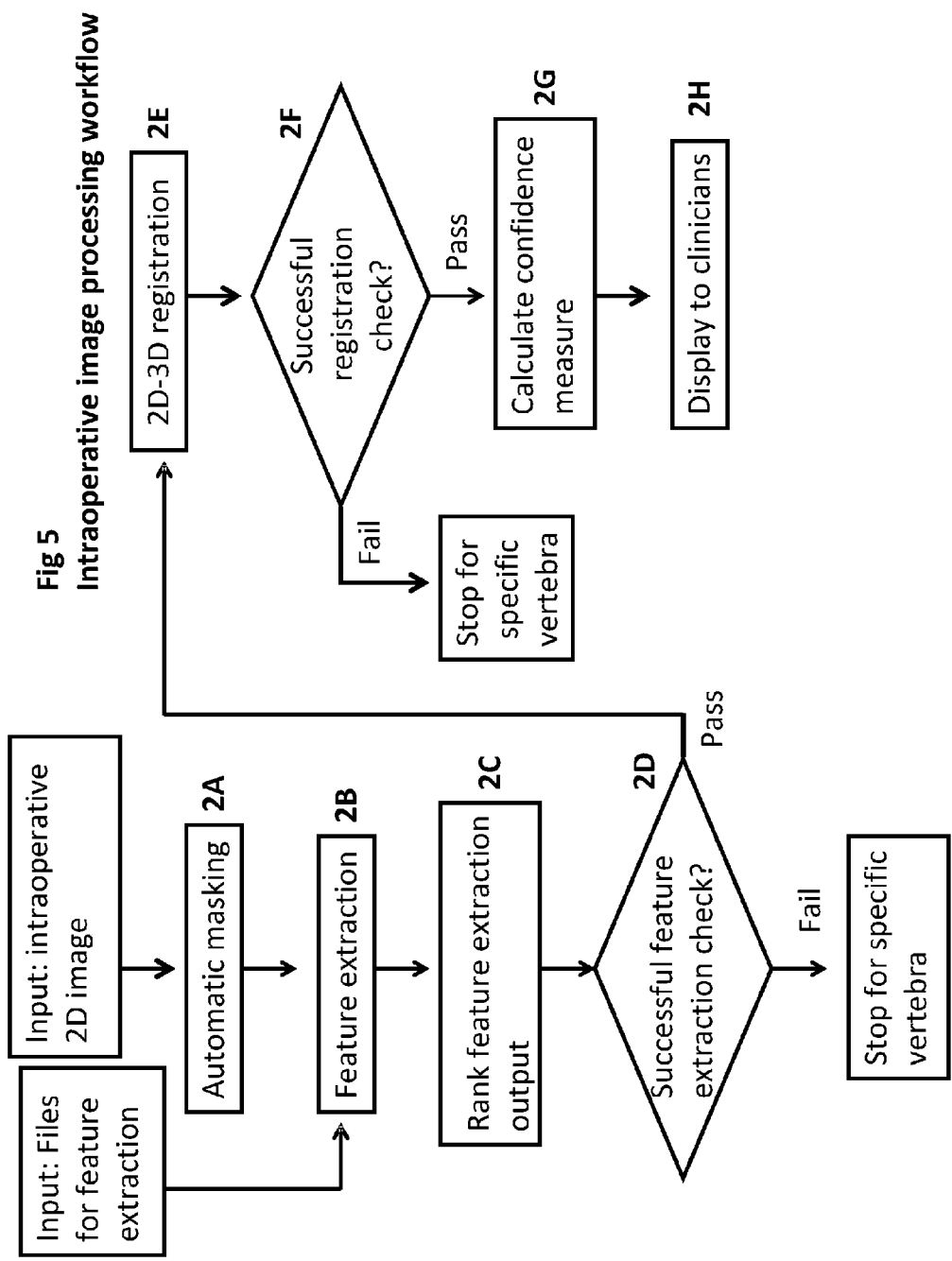
FIG. 5 is a flow diagram illustrating a registration procedure of an embodiment of the invention.

The second stage of the present embodiment is shown in FIGS. 2 and 5. FIG. 2 shows in schematic form a typical fluoroscopy set and table. Operating table 20 is provided with a C-arm 24 on opposite sides of which are an X-ray source and detector. The X-ray images from the C-arm are displayed on X-ray display 28. The patient lies on the table between the source and detector. A computer based image guided surgical system 26 receives the x-ray images on display 28 from the fluoroscopy set and generates the 2D fluoroscopy data augmented with aligned 3D image data, such as a CT scan, as shown on display 30. The IGSS 26 is controlled via user input device 32, such as a keyboard or the like.

The operation of the IGSS during the second stage of the present embodiment is shown in FIG. 5. Inputs are the intraoperative 2D fluoroscopy or x-ray image, as well as the feature sets 9044, in this case R-tables generated from the synthetic DRR images.

Step 2A first automatically masks out areas at the edge of the image which contain no (or little) information. These commonly arise due to "coning" of the x-ray beam. Coning is the process of inserting additional filters to reduce radiation exposure to patient and staff. The automatic masking operation may be carried out using a combination of thresholding, region growing from image edge seed points and a morphological dilation operator.

Figure 8:
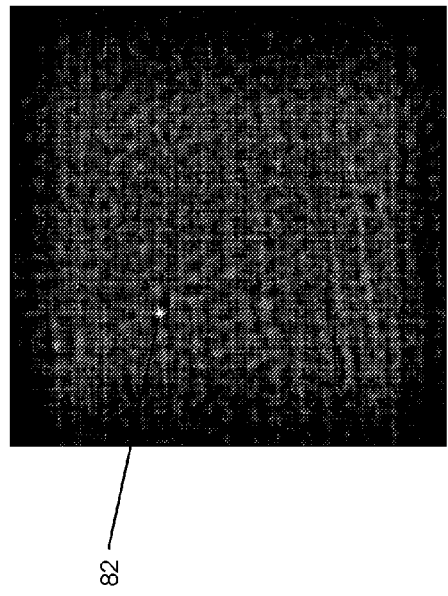
FIG. 8 is en example accumulation image from the application of a generalised Hough transform in an embodiment of the invention.

Step 2B then uses the output from step 1C previously i.e. the R-tables to apply a fast and robust feature extraction process to the masked 2D image. For example, if a generalised Hough transform is used in step 1C then the input here will be the set of R-tables representing different vertebrae, and different imaging parameters. That is, each R table represents a particular vertebra, as if it were viewed from a different imaging angle defined by the imaging parameters. Each of these R-tables will be applied to the image to produce a set of accumulation images equal in size to the number of R-tables. An example accumulation image is shown in FIG. 8.

Step 2C takes the output from step 2B and ranks the view directions in terms of which one is best able to extract each vertebra. For example, if a generalised Hough transform is used in step 1C then step 2C will assess which accumulation image best extracts each vertebra. This may be done by finding a normalised maximum value in the accumulation images for each vertebra.

One way to find the normalised maximum value of the accumulation images is as follows. Each of the accumulation images are taken in turn. The maximum intensity value V1 of an accumulation image is found. Then the pixel containing the maximum value, and a region within a predetermined number, for example 5, pixels are set to zero. The next highest value is then found within the image, V2, and the pixels within a region of 5 pixels of V2 are set to zero. This process is repeated to calculate the five highest values, V1, V2, V3, V4, and V5. The normalised maximum value then equals V1 divided by (V2+V3+V4+V5)/4.

Alternatively, another technique that may be used is to find the pixel that has the maximum value, and then to find the average intensity value of all the pixels in the accumulation image. This average value is then used to normalise the maximum value i.e. the normalised maximum value equals the maximum value divided by the average value.

The effect of either of the two techniques is to find, for each accumulation image, whether there is a maximum point which is significantly higher than the typical background intensity pixel levels in an accumulation image. In this respect, if an R-table were to perfectly match a feature in the 2D image then the accumulation image produced by the generalised Hough transform would tend to a single high value point in the image. Finding the normalised maximum value is therefore a measure of to what extent the accumulation image tends to the theoretical ideal for a perfect match, and hence can be used to discriminate which accumulation image best locates the registration feature. For example, in the example accumulation image of FIG. 8, there is clearly a single high value point 82, which indicates the position of the feature. Specifically, the high value point indicates the position of the point R of the R-table used to find the feature.

Generally, the registration feature is best located by the accumulation image with the highest normalised maximum value. However, noisy and low contrast 2D fluoroscopy images can result in the assessment of the registration feature's position being inaccurate. Therefore, it is desirable that another process of ranking the accumulation images be applied in order to improve the accuracy of step 2C.

One way of doing this is to begin by finding the first N (e.g. N=100) ranked accumulation images based on the normalised maximum intensity pixel values in each of the accumulation images. These N ranked accumulation images may then be further processed as follows: A 2D-3D registration similarity measure (for example, gradient difference, Penney, G. P., Weese, J., Little, J. A., Desmedt, P., Hill, D. L. G. and Hawkes, D. J. "*A comparison of similarity measures for use in 2D-3D medical image registration*", IEEE Trans. Med. Imag., 1998, 17(4), 586-595) is used to calculate a similarity value between the 3D image data (e.g. CT scan) and the 2D image (e.g. fluoroscopy image) for each of the first N accumulation images found. The accumulation image associated with the maximum value calculated by the similarity measure determines the start position for a subsequent 2D to 3D registration.

The overall effect of this processing is that the normalised maximum intensity is first used to find a small number of accumulation images which may provide the starting position for 2D-3D registration, and then the more accurate and robust (but computationally more expensive) similarity measure is used to make the final selection, thus accurately determining which accumulation image best extracts each vertebra.

Step 2D checks for each vertebra whether it has been successfully extracted by step 2C. This is achieved by comparing the view directions for each vertebra determined by step 2C. If two or more vertebrae have been successfully extracted then "similar" views will be obtained. A suitable threshold for "similar" views, for example could be whether they are within five degrees for each rotation parameter. Due to the large search space used, if feature extraction on each vertebra is independent then similar positions are unlikely to occur by chance. Note not all vertebrae will appear in a fluoroscopy image and so this stage determines which vertebra are within the fluoroscopy image, as well as which vertebra have been accurately extracted. If only one or fewer vertebrae are extracted then the algorithm stops.

Step 2E then takes the vertebrae which have been successfully extracted and uses knowledge of their view directions and in-plane position of where the feature was located (as determined by step 2C) to automatically provide a starting estimate for an intensity based 2D-3D registration as described in Penney et al. IPCAI 2011, referenced above. At this stage therefore, actual registration is performed, using the prior art intensity based method described in the above reference.

Step 2F is a check for registration success. For example, the final registration positions for each vertebra used in step 2E are compared. Successful registrations to different vertebra should produce very similar final positions. These will be compared using a suitable threshold, for example whether rotation parameters are within 2 degrees and in-plane translations within 2 mm. If no successful registrations are found then the algorithm ceases operation.

Step 2G calculates a confidence value for the registration. For example this value could be calculated using the relative vertebrae positional information calculated in step 2F and/or using the final value of the registration similarity value.

In more detail, a confidence value may be calculated using statistics from previous manually checked registrations as follows:

i) Let V_i be a numerical value from a registration. For example, this could be the final value of a similarity measure, or the mean change in relative vertebra positions, or another calculated value. A large number of previous registrations are available i=1, . . . , 1000 for example.

ii) T_i is a corresponding flag on whether registration i failed (F) or succeeded (S)—this would have been determined using visual inspection.

iii) The i registrations are placed into a set of bins depending on their value of V_i. Here, t_j represents the set of index values (i) for the j'th bin where V_i falls between the lower (L) and upper (U) bounds of the j'th bin, namely: L_j>V_i>U_j. The probability of a registration failure in the j'th bin can be calculated as the ratio of the cardinality of the set t_j such that T_t_j=F divided by the cardinality of all of set t_j i.e. the number of failures in the bin divided by the total number of registrations within the bin.

iv) For a new registration, the value of V_i can then be translated into a probability of a failed registration, by calculating which bin V_i belongs to and then outputting the calculated probability. Such confidence values can be calculated from a number of numerical values, and probabilities either calculated and displayed individually or 2D or 3D binning processes undertaken and combined confidence values calculated.

Finally, step 2H displays the requested information to the clinician along with the confidence value. For example this could be an overlay of the vasculature from the 3D preoperative image onto the interventional 2D fluoroscopy image.

With the above, therefore, a starting position for an intensity based 2D to 3D image registration is found by comparing feature sets from synthetic images generated from a large amount of possible viewing angles with the live 2D data, and finding which of the feature sets best matches the view shown in the 2D image. The viewing parameters that were used to generate the synthetic image the feature set of which best matched the 2D data, as well as the translational positioning data that is obtained from the matching process are then used to provide an automatic starting position for the intensity based image registration process. The above embodiment therefore addresses the above noted problem of the prior art that manual vertebra identification and alignment can be problematic and take time by the provision of an automated technique. In addition, the use of the automated technique also allows for the calculation of a confidence value in the registration, which can be displayed to the surgeon and hence provide the surgeon or other clinician with confidence that proper registration has being achieved. Moreover, replacing the prior art manual technique with embodiments of the present invention removes one of the sources of error in an image guided surgical procedure.

Various modifications, whether by way of addition, deletion or substitution may be made to the above described embodiment to provide further embodiments, any and all of which are intended to be encompassed by the appended claims.

The invention claimed is:

1. A method of determining a start position for a 2D to 3D image registration, the method comprising:
   a) obtaining characteristic feature sets characterising one or more registration features imaged in a plurality of synthetic 2D images, the plurality of synthetic 2D images having been generated from a 3D image data set, the synthetic 2D images containing the one or more registration features having been imaged according to a plurality of respective viewing parameters
   b) obtaining a 2D image to be registered with the 3D image data set;
   c) applying the characteristic feature sets to the obtained 2D image to locate one or more registration features therein; and
   d) determining which of the one or more characteristic features sets locate the one or more registration features in the obtained 2D image;
   wherein at least the viewing parameters relating to the synthetic image corresponding to the determined characteristic features sets provide information relating to a start position for a subsequent registration of the obtained 2D image to the 3D image data set.

2. The method of claim 1, wherein the registration features are one or more vertebrae.

3. The method of claim 1, wherein the obtained 2D image is a fluoroscopy image.

4. The method of claim 1, wherein the 3D image data set is obtained via a computerized tomography (CT) scan.

5. The method of claim 1, wherein the characteristic feature sets are R tables for use with a generalized Hough transform, wherein the applying comprises generating accumulation images by applying the R-tables to the obtained 2D image using the generalized Hough transform.

6. The method of claim 5, wherein the determining comprises ranking the accumulation images to determine which R table best locates the registration feature in the obtained 2D image.

7. The method of claim 6, wherein the first N ranked accumulation images are further processed, the further processing comprising:
   a) calculating a similarity value between the 3D image data set and the obtained 2D image for each of the N ranked accumulation images by means of a 2D-3D registration similarity measure; and
   b) determining the start position for a subsequent 2D to 3D registration based on the accumulation image associated with the maximum calculated similarity value.

8. The method of claim 1, further comprising checking that two or more registration features are located in the obtained 2D image.

9. The method of claim 8, further comprising, for the two or more registration features, checking that the viewing parameters relating to the characteristic feature sets that located the registration features are within a predetermined distance of each other.

10. The method of claim 1, further comprising performing 2D to 3D image registration using the determined start position information.

11. The method of claim 10, further comprising checking that registration parameters achieved for different registration features are within a predetermined distance.

12. The method of claim 10, further comprising calculating a confidence value for the registration(s), and displaying the confidence value to the user.

13. A method of generating characteristic feature sets characterising a registration feature for use in the method of claim 1, the method comprising:
   a) generating a plurality of synthetic 2D images from a 3D image data set, the synthetic 2D images containing one or more registration features imaged according to a plurality of respective viewing parameters;
   b) generating characteristic feature sets from the synthetic 2D images characterising the registration features imaged therein; and
   c) storing the generated characteristic feature sets.

14. The method of claim 13, wherein the registration features are one or more vertebrae.

15. The method of claim 13, wherein the 3D image data set is obtained via a computerised tomography (CT) scan.

16. The method of claim 13, wherein the characteristic feature sets are R tables for use with a generalised Hough transform.

17. An image guided surgical system, comprising:
   a 2D imaging system arranged in use to obtain a 2D image to be registered with a 3D image data set; and
   a processor, arranged in use to:
   a) obtain characteristic feature sets characterising one or more registration features imaged in a plurality of synthetic 2D images, the plurality of synthetic 2D images having been generated from the 3D image data set, the synthetic 2D images containing the one or more registration features having been imaged according to a plurality of respective viewing parameters;
   b) apply the characteristic feature sets to the obtained 2D image to locate one or more registration features therein; and
   c) determine which of the one or more characteristic features sets locate the one or more registration features in the obtained 2D image;
   wherein the viewing parameters relating to the synthetic image corresponding to the determined characteristic feature sets provide information relating to a start position for registration of the obtained 2D image to the 3D image data set.

18. The system of claim 17, wherein the registration features are one or more vertebrae.

19. A system for generating characteristic feature sets characterising a registration feature for use with the system of claim 17, the system comprising:
   a processor; and
   a computer readable storage medium, the computer readable storage medium storing one or more programs so arranged such that when executed by the processor it/they cause the processor to:
   a) generate a plurality of synthetic 2D images from a 3D image data set, the synthetic 2D images containing one or more registration features imaged according to a plurality of respective viewing parameters;
   b) generate characteristic feature sets from the synthetic 2D images characterising the registration features imaged therein; and
   c) store the generated characteristic feature sets.

20. The system of claim 19, wherein the one or more programs further causes the processor to generate characteristic feature sets characterising a registration feature for use in the method of claim 1, the method comprising:
   (a) generating a plurality of synthetic 2D images from a 3D image data set, the synthetic 2D images containing one or more registration features imaged according to a plurality of respective viewing parameters;
   (b) generating characteristic feature sets from the synthetic 2D images characterising the registration features imaged therein; and
   (c) storing the generated characteristic feature sets;
   and wherein the system includes one or more of features (i) to (iii), below:
   (i) the registration features are one or more vertebrae;
   (ii) the 3D image data set is obtained via a computerised tomography (CT) scan; and
   (iii) the characteristic feature sets are R tables for use with a generalised Hough transform.

* * * * *